(12) United States Patent
Lin

(10) Patent No.: US 7,935,334 B2
(45) Date of Patent: May 3, 2011

(54) PROBIOTICS AS ALTERNATIVE MEDICINES AGAINST INFECTIOUS DISEASES

(75) Inventor: Jhy-Jhu Lin, Potomac, MD (US)

(73) Assignee: Imagilin Technologies, LLC, Frederick, MD (US)

( * ) Notice: Subject to any disclaimer, the term of this patent is extended or adjusted under 35 U.S.C. 154(b) by 986 days.

(21) Appl. No.: 11/493,859

(22) Filed: Jul. 26, 2006

(65) Prior Publication Data

US 2007/0020328 A1    Jan. 25, 2007

Related U.S. Application Data

(60) Provisional application No. 60/705,730, filed on Aug. 5, 2005.

(51) Int. Cl.
| | |
|---|---|
| A61K 45/00 | (2006.01) |
| A01N 25/34 | (2006.01) |
| A01N 63/00 | (2006.01) |
| C12N 1/20 | (2006.01) |
| C12N 11/02 | (2006.01) |
| C12N 11/10 | (2006.01) |

(52) U.S. Cl. .................. 424/93.45; 424/282.1; 424/408; 435/177; 435/178; 435/252.9; 435/822

(58) Field of Classification Search ........................ None
See application file for complete search history.

(56) References Cited

U.S. PATENT DOCUMENTS

| | | | |
|---|---|---|---|
| 4,804,542 A | 2/1989 | Fischer et al. | |
| 5,501,857 A | 3/1996 | Zimmer | |
| 5,840,318 A * | 11/1998 | Marshall et al. | ........... 424/282.1 |
| 5,968,569 A | 10/1999 | Cavadini et al. | |
| 6,500,463 B1 * | 12/2002 | van Lengerich | .............. 424/499 |
| 6,551,633 B2 | 4/2003 | Couzy et al. | |
| 6,780,447 B2 | 8/2004 | Raczek | |
| 6,827,957 B2 | 12/2004 | Paluch et al. | |
| 6,835,397 B2 | 12/2004 | Lee et al. | |
| 7,067,150 B2 | 6/2006 | Farber et al. | |
| 2003/0049240 A1 | 3/2003 | Ballevre et al. | |
| 2003/0109025 A1 | 6/2003 | Durand et al. | |
| 2003/0147858 A1 | 8/2003 | Renaud et al. | |
| 2003/0165472 A1 | 9/2003 | McGrath et al. | |
| 2004/0126356 A1 | 7/2004 | Pang et al. | |
| 2004/0197352 A1 | 10/2004 | Ranganathan | |
| 2006/0008511 A1 | 1/2006 | Lin | |

OTHER PUBLICATIONS

Walker, Richard and Buckley, Merry. Probiotic Microbes the scientific Basis. American Acedemy of Microbiology symposium, Baltimore, Maryland, Nov. 5-7, 2005.
Tuomola, Elina et al., quality assurance criteria for probiotic bacteria. American Journal Clinical Nutrition 2001; 73(suppl):393S-8S.
Talwalkar, Akshat et al. The role of oxygen in the viability of probiotic bacteria with reference to *L. acidophilus* and *Bifidobacterium* spp. Current Issues Interest Microbiology, (2004) 5:1-8.
Perdigon, Gabriela et al. Lactic acid bacteria and their effect on the immunesystem. Current Issues Interest Microbiobiology. (2001) 2(1): 27-42.
Lillehoj, H.S. et al. Recent progress on the cytokine regulation of intestinal immune responses to Eimeria. Ancillary Scientists Symposium, Poultry Science Assoc. 2004 Poultry Science 83:611-623.
Isolauri, E. Probiotics for infectious diarrhoea. Gut 2003:52:436-437.
Dalloul, R.A. et al. Immunopotentiating effect of a fraxinea-derived lectin on chickne immunity and resistance to coccidiosis. 2006 Poultry Science 85:44 6-451.
Fuller, R. Probiotics in man and animals. Journal of Applied Bacteriology 1989, 66, 365-378.

* cited by examiner

*Primary Examiner* — Deborah K. Ware

(57) ABSTRACT

An exemplary embodiment providing one or more improvements includes feeding animals with probiotic microbes encapsulated in a mixture of xanthan gum and chitosan, or in gelatin, specifically *Pediococcus acidilactici* and *Saccharomyces boulardii*. Such encapsulation protects the viability of the probiotic microbes against unfavorable temperatures. An exemplary embodiment providing one or more improvements includes methods of using viable probiotics in therapy of birds and mammals infected with infectious diseases. Probiotics acted as adjuvants in stimulating antibody reaction and stimulated a cellular immunity response. In particular, probiotics were shown to reduce the number of viable oocytes from fecal samples, stimulate antibody production, and stimulate of proliferation of splenocytes in chickens infected with *Elimeria*. In addition, probiotics were shown to relieve symptoms of parvovirus infection in dogs.

9 Claims, 6 Drawing Sheets

PROBIOTICS AS ALTERNATIVE MEDICINES AGAINST INFECTIOUS DISEASES

CROSS-REFERENCE(S)

This application claims priority from application Ser. No. 60/705,730 filed Aug. 5, 2005, Ser. No. 11/177,264, filed Jul. 7, 2005, and Ser. No. 60/585,941, filed Jul. 8, 2004.

STATEMENT REGARDING FEDERALLY SPONSORED RESEARCH OR DEVELOPMENT

Not Applicable.

REFERENCE TO A "MICROFICHE APPENDIX"

Not Applicable.

BACKGROUND

Description of Related Art Including Information Disclosed Under 37 CFR 1.97 and 37 CFR 1.98

Probiotics are described as "live microorganisms, which, when administered in adequate amounts, confer a health benefit on the host" (reports of the United Nations Food and Agricultural Organization and the World Health Organization, Alternative Medicine 2001). Probiotics are widely applied as nutritional supplements in animals and humans. For example, yeast is used as a nutrient supplement for livestock, and yogurt with lactic acid bacteria-*Lactobacillus* and/or *Bifidobacterium* is commonly used to prevent and cure diarrhea-related gastrointestinal (GI) infectious diseases (Alvaez, et al, 2001; Fuller 1989; Majamaa, et al 1995). Multiple unique properties of probiotics such as anti-infectious properties, immune modulatory effects, enhanced barrier functions, metabolic effects and alternations of intestinal mobility or function make probiotics an effective type alternative medicine for animals and humans (Walker and Buckley, 2006).

Although probiotic products like short chain fatty acids (SCFA), cell wall peptidoglycan and short chain DNA fragments containing CpG sequences can have beneficial probiotics effects, the administration of live microorganisms to animals and humans remain to be the core application and research studies of probiotics (Walker and Buckley, 2006). In order to have the maximum effects of probiotics on animals and humans, one has to administrate live bacteria to reach gastrointestinal tracts for multiplication (Kailasapatha and Chin 2000). *Lactobacillus* spp and *Bifidobacterium* spp are two most commonly probiotics described in scientific literature and in commercial products. Both *Lactobacillus* spp and *Bifidobacterium* spp are facultative anaerobic bacteria. Most species (or strains) of *Lactobacillus* and *Bifidobacterium* are sensitive to the exposure of oxygen (Gomes et al, 1995: Talwalkar and Kailasapathy, 2004) and high temperature. It is difficult to maintain the viability of *Lactobacillus* and *Bifidobacterium* at room temperature under consistent open and closure operations. Therefore, variable results are often described, especially for commercially available products that are required to have long term storage and shipping in various temperature (Tuomola et al, 2001).

U.S. Pat. No. 5,968,569 discloses a pet food product of a gelatinized starch matrix including a probiotic micro-organism. Specifically disclosed are *Saccharomyces* and *Pediococcus acidilactici*.

U.S. Pat. No. 6,551,633 discloses a milk based powder for pets which includes lactase and lactose. Also disclosed are the probiotic organisms of U.S. Pat. No. 5,968,569.

U.S. Pat. No. 6,780,447 discloses animal foods comprising sorbic acid and live or dead microorganisms. A very large number of species is disclosed including *P. acidilactici*.

U.S. Pat. No. 6,827,957 discloses animal foods of specific formulation having a soft inner component and a hard shell along with probiotics. Specifically, *Saccharomyces* is disclosed.

U.S. Pat. No. 6,835,397 discloses an encapsulated yeast including a variety of probiotics including *Saccharomyces. boulardii* and *Pediococcus. acidilactic* (sic).

US Pub. Pat. Applic. 2003/0049240 discloses a method for treating *helicobacter* infections including the use of *Lactobacillus* and *Bifidobacterium*.

US Pub. Pat. Applic. 2003/0109025 discloses methods for creating particles containing coated living micro-organisms.

US Pub. Pat. Applic. 2004/0197352 discloses a prebiotic composition which reduces creatine and BUN and includes a variety of microbial species.

US Pub. Pat. Applic. 2003/0165472 discloses a method for the storage and delivery of microorganisms.

US Pub. Pat. Applic. 2006/0008511, incorporated herein by reference, discloses probiotic microbes encapsulated in a mixture of xanthan gum and chitosan, or in gelatin.

REFERENCES

Alvaez, S., Herrero, C., Bru, E., Perdigon, G. 2001. Effect of *Lactobacillus casei* and yogurt administration on prevention of *Pseudomonas aeruginosa* infection in young mice. J. food Prot. 64: 1768-1774.

Dalloul, R. A., H. S. Lillehoj, J.-S. Lee, S.-H. Lee, and K.-S. Chung. 2006. Immunopotentiating effect of a Fomitella fraxinea-derived lectin on chicken immunity and resistance to coccidiosis. Poult. Sci. 85:446-451.

Fuller, R. 1989. Probiotics in man and animals. A review. J. Appl. Bacteriol 66:365-78.

Gomes A. M. P., Malcata F. X., Klaver F. A. M., Grande H. J. 1995 Incorporation and survival of *Bifidobacterium* sp. strain Bo and *Lactobacillus acidophilus* strain Ki in a cheese product. Netherlands milk and dairy journal vol. 49: 71-95.

Isolauri, E. 2003. Probiotics for infectious diarrhea. Gut 52: 436-437.

Kailasapatha K, Chin J. 2000. Survival and therapeutic potential of probiotic organisms with reference to *Lactobacillus acidophilus* and *Bifidobacterium* spp. Immunol Cell Biol. 78: 80-88.

Lillehoj, H. S., W. Min, and R. A. Dalloul. 2004. Recent progress on the cytokine regulation of intestinal immune responses to Eimeria. Poult. Sci. 83:611-623.

Majamaa, H., Isolauri, E., Saxelin, M., Vesikari, T. 1995. Lactic acid bacteria in the treatment of acute rotavirus gastroenteritis. J. Pediatric Gastroenterol Nutr 20: 333-339.

Perdigon, G., Fuller, R., Raya, R. 2001. Lactic acid bacteria and their effect on the immune system. Curr Issues Intest Microbiol. 2(1): 27-42.

Talwalkar A, Kailasapathy K. 2004 The role of oxygen in the viability of probiotic bacteria with reference to *L. acidophilus* and *Bifidobacterium* spp. *Curr Issues Intest Microbiol.*: 5(1):1-8.

Tuomola, E., Crittenden, R., Playne, M., Isolauri, E., and Salminen, S. 2001 Quality assurance criteria for probiotic bacteria. Am J Clin Nutr 73(suppl): 393S-398S.

Walker, R. and Buckley, M., 2006 "Probiotic Microbes: The Scientific Basis" 2006

A report from the American Academy Microbiology, page 1-28. by Pensare Design Group.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following embodiments and aspects thereof are described and illustrated in conjunction with systems, tool and methods which are meant to be exemplary and illustrative, not limiting in scope. In various embodiments, one or more of the above-described problems have been reduced or eliminated, while other embodiments are directed to other improvements.

Embodiments disclosed include a preparation for pets comprising probiotic microbes encapsulated in a mixture of xanthan and chitosan gums. Embodiments disclosed include a preparation for pets comprising probiotic microbes encapsulated in a gelatin capsule. In embodiments the probiotic microbes comprise *Saccharomyces* yeast and lactic acid bacteria. In embodiments the probiotic microbes comprise yeast. In embodiments the probiotic microbes comprise lactic acid bacteria. In embodiments the yeast is *Saccharomyces*. In embodiments the lactic acid bacteria is *Pediococcus*. In embodiments the *Saccharomyces* yeast is *Saccharomyces cereviase boulardii* also termed *Saccharomyces boulardii*. In embodiments the lactic acid bacteria is *Pediococcus acidilactici*. In embodiments the xanthan gum concentration is from about 0.2 percent weight by volume to about 2 percent weight by volume and the concentration of chitosan gum is about 0.1 percent weight by volume to 1.0 percent weight by volume and the pH is from about 2 to about 7. In embodiments the xanthan gum concentration is from about 01.25 percent weight by volume and the concentration of chitosan gum is about 0.4 percent weight by volume and the pH is about 4.15. Embodiments include the process of treating infectious gastrointestinal disease in birds and mammals in need of such treatment which comprise the step of feeding the bird or mammal in need of treatment encapsulated probiotic microbes or include the probiotics in animal food or in animal treats. Embodiments include the process of enhancing immune responses against antigens in birds and mammals which comprise the step of feeding the bird or mammal in need of treatment encapsulated probiotic microbes or include the probiotics in animal food or in animal treats.

DETAILED DESCRIPTION

Viable lactic acid bacteria and yeasts used in probiotics for pets, such as dogs and cats, are encapsulated and protected by the microbial biopolymers xanthan gum and chitosan. Xanthan gum is a polysaccharide gum which dissolves readily in water with stirring to give highly viscous solutions at low concentrations. It forms strong films on evaporation of aqueous solutions and is resistant to heat degradation. Chitin is a polysaccharide consisting predominately of unbranched chains of N-acetyl-glucosamine residues. Chitosan is deacylated chitin, a polymer often used in water treatment, photographic emulsion, in improving the dyeability of synthetic fibers and fabrics and in wound-healing preparations.

Probiotic microbes were encapsulated with an aqueous solution containing 0.5 to 2.5 percent (weight by volume) xanthan gum and 0.2 to 0.8 percent (weight by volume) chitosan. The pH of the solution was from 2.0 to 7.0. A preferred solution contained 1.25 percent (weight by volume) xanthan and 0.4 percent (weight by volume) chitosan at a pH of 4.15. Viable microbial cells are encapsulated at up to 1010 colony forming units (cfu) per ml.

Encapsulation of viable probiotic microbes in the mixture of xanthan gum and chitosan has the advantage of protecting the viability of the microbes, of delivering the proper dosage of viable probiotic microbes to the pet or dog which is being fed, and of facilitating the feeding of the probiotic microbes. Dogs and cats do not reject the probiotic microbes when they are encapsulated in a mixture of xanthan gum and chitosan.

Without wishing to be held to this explanation, the inventors suggest the observed efficacy of the chitosan and xanthan gum solution in encapsulation of probiotic microbes is due to the formation of a xanthan-chitosan complex. The mixture of two oppositely charged polyelectrolytes in aqueous solution results in formation of a polyelectrolyte complex due to the electrostatic attraction of oppositely charged polymers. It is postulated that at moderate pH values the xanthan gum is predominately associated with a large number of net negative charges, while chitosan is associated with a large number of net positive charges. The two polymers with opposite net charges therefore bind together forming a stable complex and a strong gel. Relatively high pH values deionize the amino groups on the chitosan with resulting less stable binding between the two polymers and less strong capsule.

Figure 1:
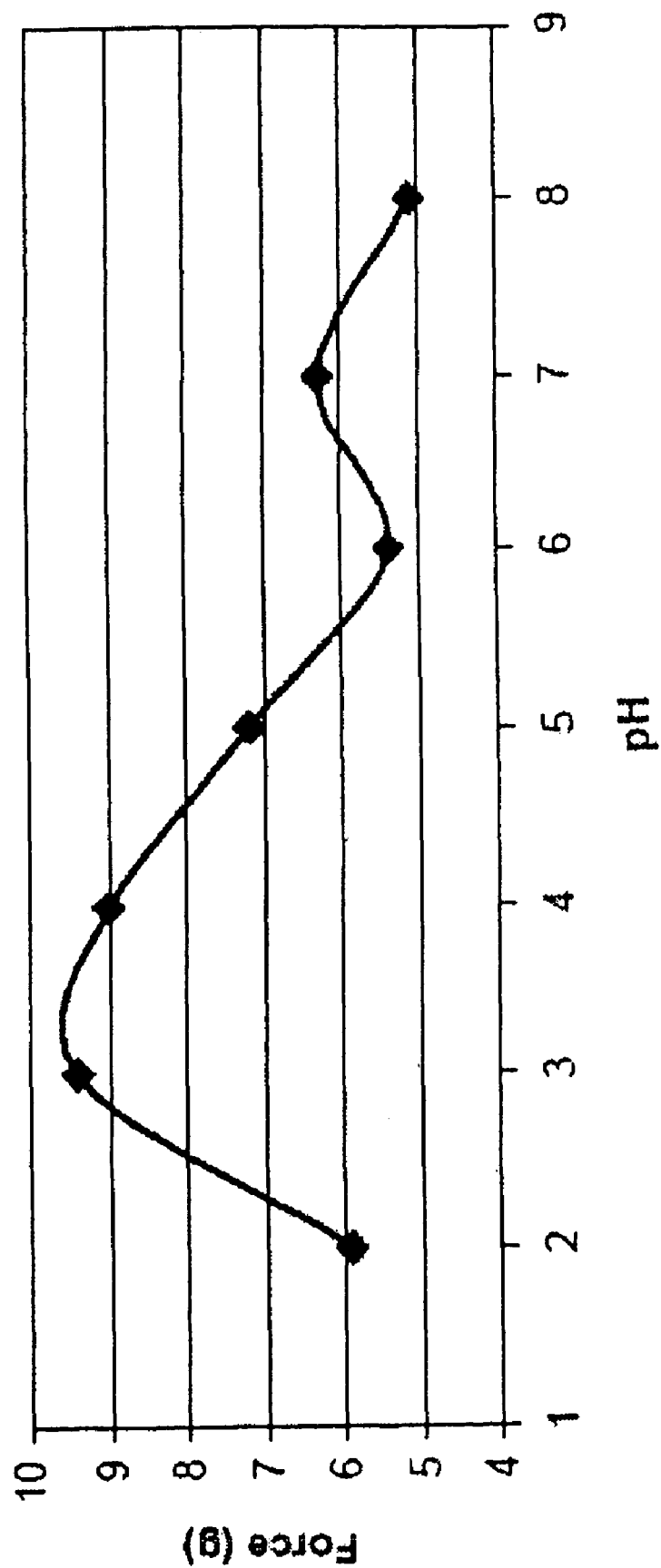
FIG. 1 shows the relationship between pH and capsule hardness.

FIG. 1 is a graph showing the capsule hardness at pH values from 2 to 8. Capsules were formed as in the preferred process above. Capsule hardness or mechanical strength was measured at a variety of pH values using TA.XT2i, using a 5 kg load cell and a distance of 1 mm. FIG. 1 showed that the hardness of the capsules peaks in the pH range of 3 to 4, and was relatively low at pH 6 to 8. The data of FIG. 1 are consistent with the above theoretical discussion of the formation of a chitosan-xanthan gum complex.

Figure 2:
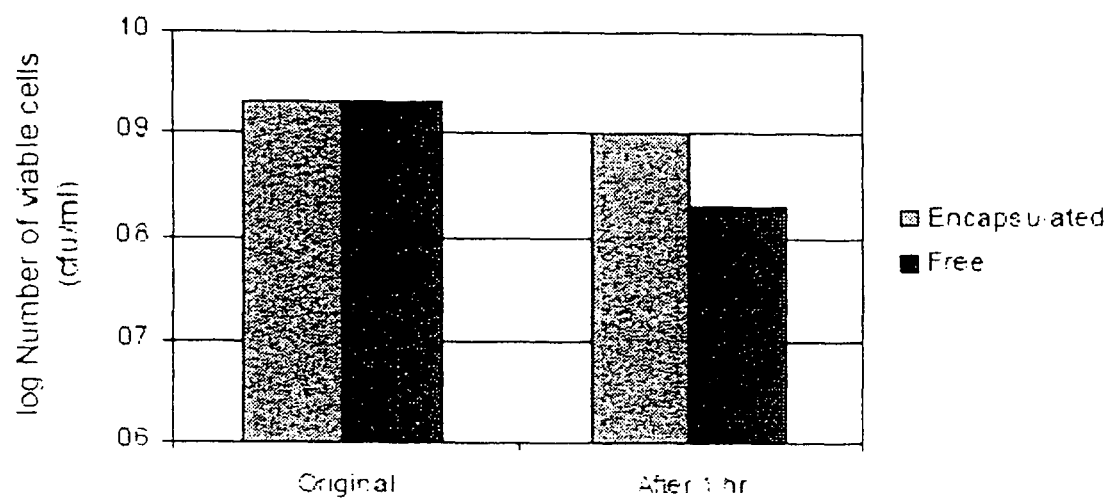
FIG. 2 shows the relationship between viability of encapsulated and unencapsulated probiotic microbes and reduced temperature.

FIG. 2 shows the effect of low temperature on the viability of encapsulated and unencapsulated microbes. Encapsulated and unencapsulated microbes were held for one hour at 0° C. The number of unencapsulated viable microbes declined from about $10^{9.3}$ cfu/ml to about $10^{8.3}$ cfu/ml. The number of encapsulated viable microbes declined from about $10^{9.3}$ cfu/ml to about $10^9$ cfu/ml. FIG. 2 shows the protective effect of encapsulation against low temperature.

Figure 3:
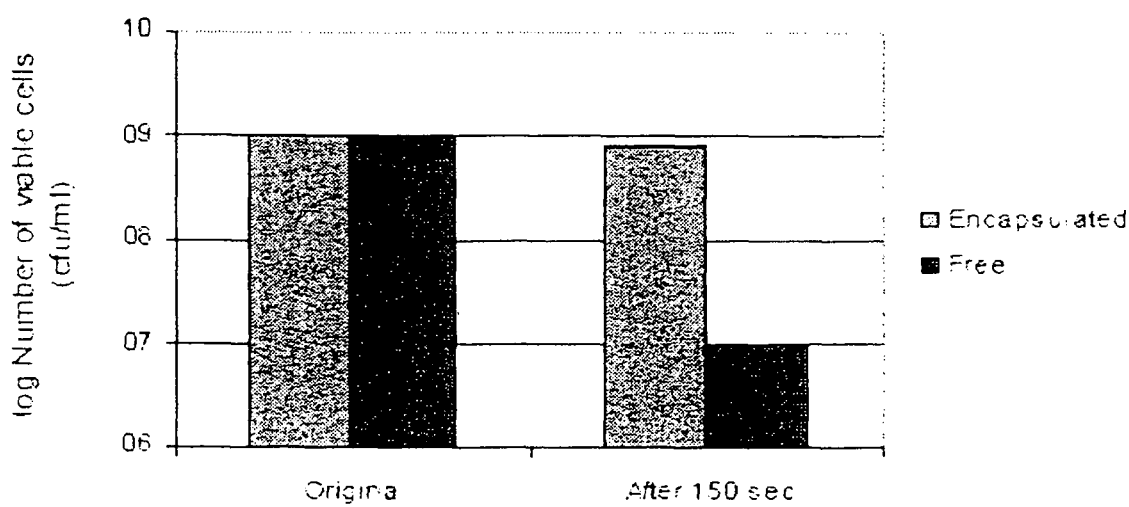
FIG. 3 shows the relationship between viability of encapsulated and unencapsulated probiotic microbes and elevated temperature.

FIG. 3 shows the effect of high temperature on the viability of encapsulated and unencapsulated microbes. Encapsulated and unencapsulated microbes were held for 150 seconds at 60° C. The number of unencapsulated viable microbes declined from about $10^9$ cfu/ml to about $10^7$ cfu/ml. The number of encapsulated viable microbes declined from about $10^9$ cfu/ml to about $10^{8.9}$ cfu/ml. FIG. 3 shows the protective effect of encapsulation against high temperature.

Figure 4:
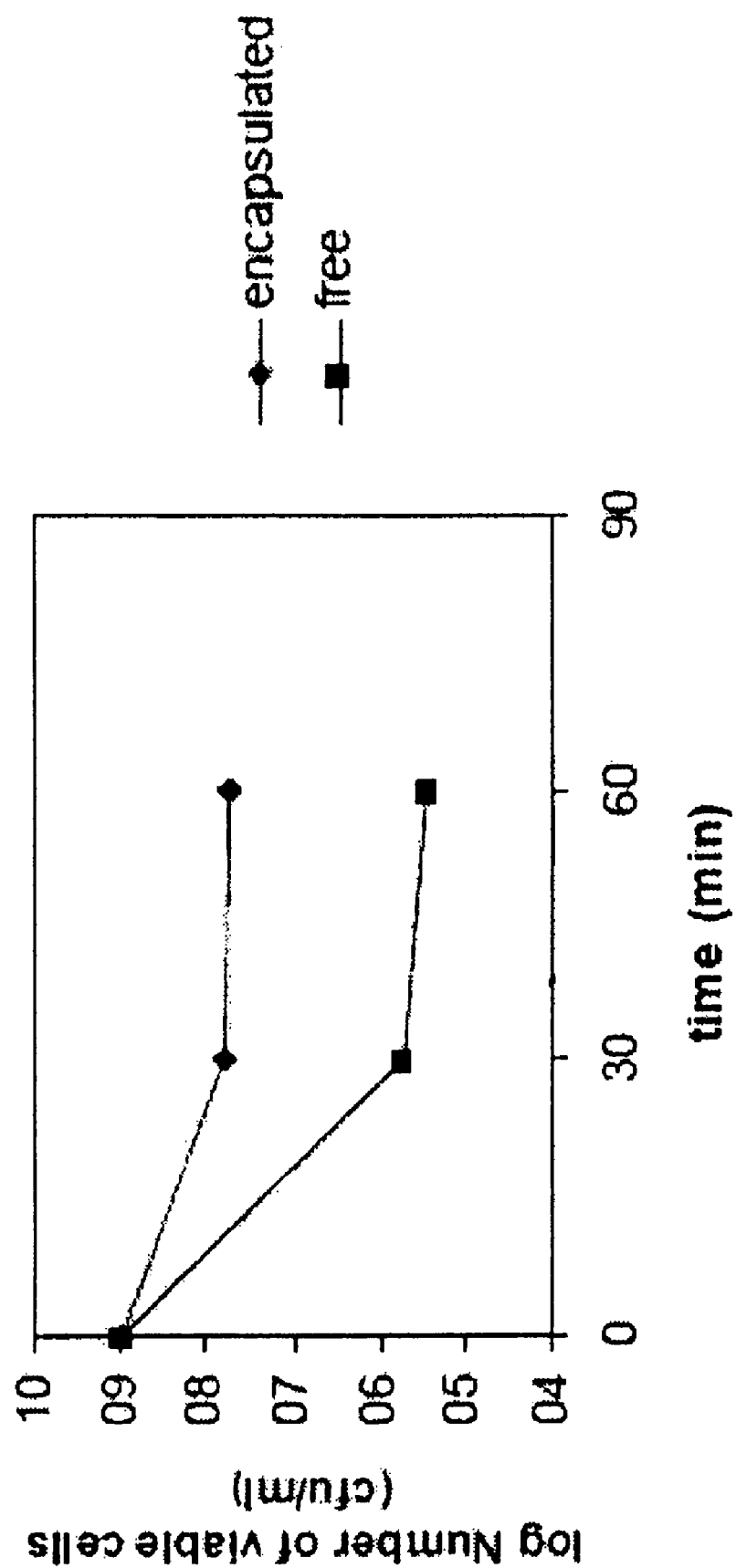
FIG. 4 shows the relationship between viability of encapsulated and unencapsulated probiotic microbes and time of exposure to pH 2.

FIG. 4 shows the effect of low pH on the viability of encapsulated and unencapsulated microbes. Encapsulated and unencapsulated microbes were held from 0 to 60 minutes at pH 2. The number of unencapsulated viable microbes declined from about $10^9$ cfu/ml to about $10^{5.7}$ cfu/ml after 30 minutes and to about $10^{5.5}$ cfu/ml after 60 minutes. The number of encapsulated viable microbes declined from about $10^9$ cfu/ml to about $10^{7.8}$ cfu/ml at both 30 and 60 minutes. FIG. 4 shows the protective effect of encapsulation against low pH.

or *Pediococcus acidilactici* containing commercial feed from day one. Five diets were formulated based on *Pediococcus acidilactici* levels as percentage of basal feed: 0%, 0.01%, 0.05%, 0.1%, and 0.4%. At day ten, all birds except for the control (no *Pediococcus acidilactici*, no infection) were orally infected with either 5,000 sporulated oocysts of *Eimeria acervulina*. Bird body weights were taken at 0, 6, & 9 days post infection (dpi) and weight gains were calculated. Fecal materials were collected for 4 days, from 6 to 9 days post infection, in small buckets for oocyst counting.

Differences between experimental treatments were tested by variance analysis (ANOVA) using the statistical program GRAPHPAD INSTAT, a trademark for statistical software owned by GraphPad Software, Inc., San Diego, Calif. Differences were considered significant at a probability $P<0.05$. Mean values were then compared by the Dunnett Comparison Test.

TABLE 1

Effects of *Pediococcus acidilactici* on growth and on oocysts in the feces from broilers infected with *Eimeria acervulina*.

A. Weight gain in grams from 1 to 9 days post infection with 5,000 *Eimeria acervulina* oocysts.

| Group | 1 | 2 | 3 | 4 | 5 | 6 |
|---|---|---|---|---|---|---|
| Dose in Oocytes | 0 | 5,000 | 5,000 | 5,000 | 5,000 | 5,000 |
| % *P. acidilactici* | 0 | 0 | 0.01 | 0.05 | 0.1 | 0.4 |
| Av. weight gain g. | 396 | 343 | 362 | 366 | 395 | 382 |
| Std. Deviation | 45 | 45 | 51 | 58 | 36 | 44 |

B. *Eimeria acervulina* oocyte shedding, above groups.

| Ave. × $10^8$ | 0 | 2.65 | 1.97 | 2.39 | 1.39 | 2.10 |
|---|---|---|---|---|---|---|
| Std. Deviation | | 0.67 | 0.50 | 0.27 | 0.23 | 0.60 |

Probiotics as alternative medicines against infectious parasitic diseases of broiler chickens Avian coccidiosis is the major parasitic disease of poultry causing mortality, malabsorption, inefficient feed utilization, impaired growth rate in broilers and reduced egg production in layers (Lillehoj et al., 2004). The most prominent symptom of avian coccidiosis is growth retardation characterized by reduced weight gains or even weight loss in severe cases, causing a major economic impact to the poultry industry (Dalloul and Lillehoj, 2006). Drugs and live vaccines are the two main control measures of disease; however, due to increasing concerns with prophylactic drug use and high cost of vaccines, alternative control methods are needed. For *Eimeria*-infected-broiler chickens, although the stimulation of antibody production was observed, the increase of cellular immune responses is the key to control the diseases (Dalloul and Lillehoj, 2004). Recent progress in probiotics research demonstrates that live bacteria can influence host humoral immunity against enteric diseases like rotavirus, *E. coli*, and *Salmonella* (Isolauri, E. 2003; Majamaa, et al 1995; Perdigon, et al 2001). In order to apply probiotics as an effective alternative medicine against *Eimeria*-infected broiler chickens one has to show the good effects of both humoral and cellular immunity in probiotics-fed, *Eimeria*-infected broiler chickens.

Examination of potential toxic effects of probiotics on *Eimeria*-infected broiler chickens Day-old broiler chicks were housed in brooders at 15-20 birds per group and fed either control, only commercial feed, Before one can apply any reagents as the potential medicines, elimination of toxic side effects is the crucial before one would apply the reagents for efficacy study. *P. acidilactici* is a natural microorganisms in GI tracts of animals and humans, and has not been described in literature to have significantly toxic effects. To investigate any potential toxic effects of *P. acidilactici* on broiler chickens, we fed broiler chickens or *E. acervulina*-infected chickens 0.01% to 0.4% of *P. acidilactici*. As shown in Table 1A, no weight loss or bird death was observed from the broiler chickens fed only with *P. acidilactici* or those infected with *E. acervulina* and fed with *P. acidilactici*. Furthermore, the *Eimeria*-infected broiler chickens fed with mixtures of probiotics-*P. acidilactici* and *Saccharomyces boulardii* in the 0.01% and 1.0% groups, and *Eimeria acervulina* infected groups showed higher body weight gains during the infection period (Table 1A). For the whole process of experiments, we did not see differences in the major organs (livers, hearts, kidneys, spleens) after feeding the chickens with probiotics. These and similar results demonstrated that *Eimeria* infected broiler chickens showed no detectable morphological differences either fed with *P. acidilactici* up to 40 folds (ranged from 0.01% to 0.4%) or with mixtures of *P. acidilactici* and *S. boulardii* ranging from 0.01% to 1.0%.

Figure 7:
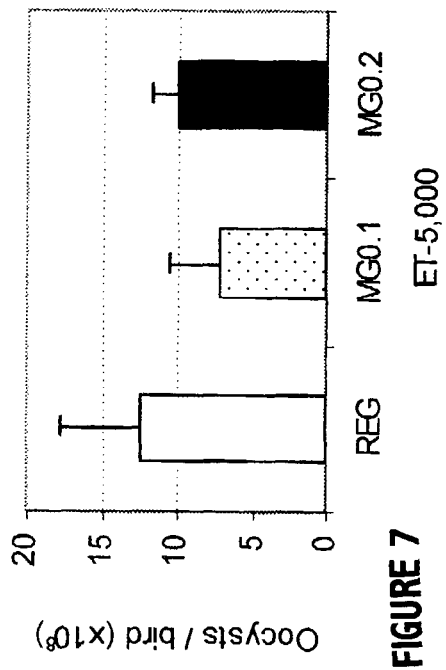
FIG. 7 is a graph of fecal oocytes shed by birds infected by *E. acervullina*.

To demonstrate that *P. acidilactici* can be used against *Eimeria* infected broiler chickens, we fed chickens with/without *P. acidilactici* and then orally infected them with sporulated oocysts of *Eimeria tellena* (*E. tellena*). Interestingly, *E. tellena* infected chickens fed with *P. acidilactici* showed a reduction of oocysts in a range of 20% to 40% from control broiler chickens (FIG. 7). Similarly, we observed the oocysts reduction either in a range of 30% to 50% from broiler chickens infected with *E. acervulina* infected and fed with mixtures of *P. acidilactici* and *S. boulardii* or in a range of 10% to 20% from broiler chickens infected with *E. tellena* and fed with mixtures of *P. acidilactici* and *S. boulardii* (FIG. 8)). These results showed probiotics have the effects on reduction of pathogens or parasites in animals Stimulation of humoral immune responses on *Eimeria*-infected, probiotics-fed broiler chickens.

Figure 5:
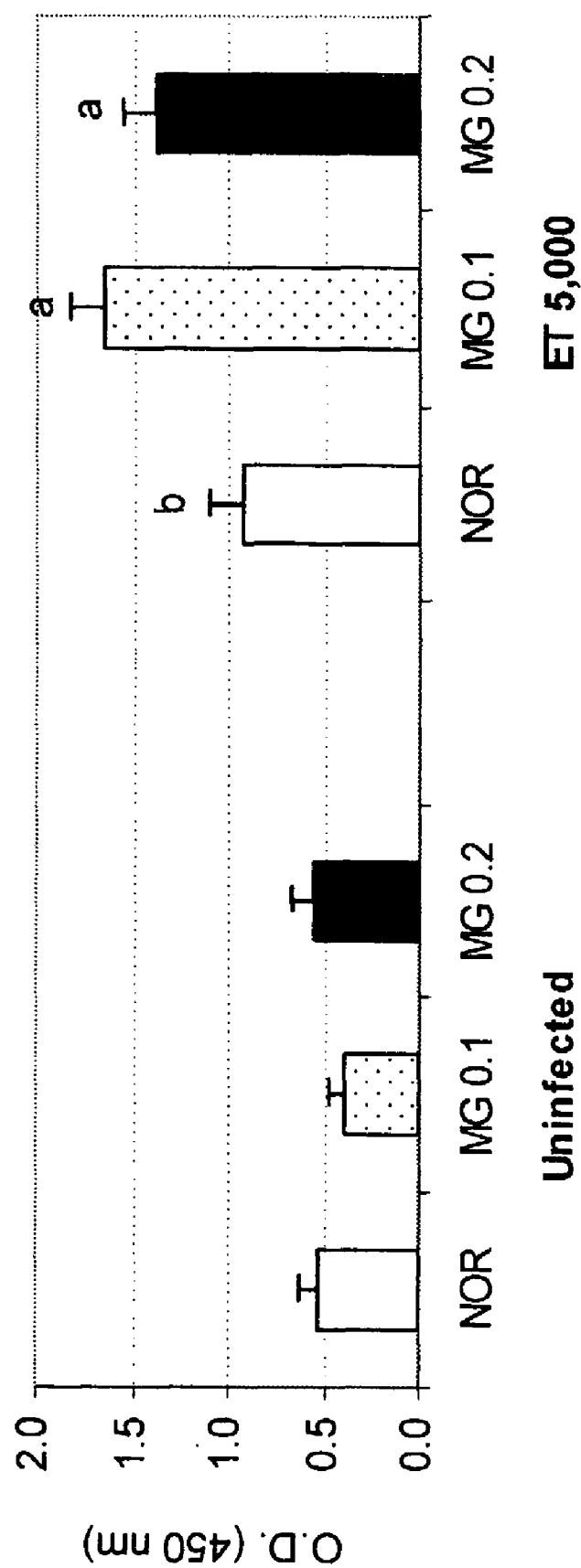
FIG. 5 is a graph showing the effect of probiotics on antibody response.

FIG. 5 shows Anti-EtMIC2 antibody response of broilers fed non-probiotic (NOR), 0.1% or 0.2% Mixtures of *P. acidilactici* and *S. boulardii* supplemented diets for 21 days (MG0.1 and MG0.2 respectively). Birds were either uninfected or infected with 5,000 *E. tenella* oocysts at day 12 post-hatch and sera sampled 10 days post infection. Each bar represents the mean±S.D. (N=3). Means lacking common superscripts differ in uninfected or infected chickens ($P<0.05$).

To assess antibody responses to *Eimeria* antigen, EtMIC2, one of *Eimeria* microneme protein genes that have been cloned and characterized at the molecular level (Dalloul et al, 2006) was used in this study. ELISAs were used to determine the antibody production from serum collected from chickens. Induction of antibody response upon ET infection was evident in all infected groups. Moreover, in *P. acidilactici*-fed birds, significantly ($P<0.05$) higher serum *Eimeria*-specific Ab levels were detected in infected birds when compared to those of birds without probiotics (FIG. 5). These results clearly demonstrate that *P. acidilactici* is able to stimulate humoral immune responses against specific infectious parasites in broiler chickens.

Systemic cellular immune responses: Lymphocyte proliferation.

Figure 6:
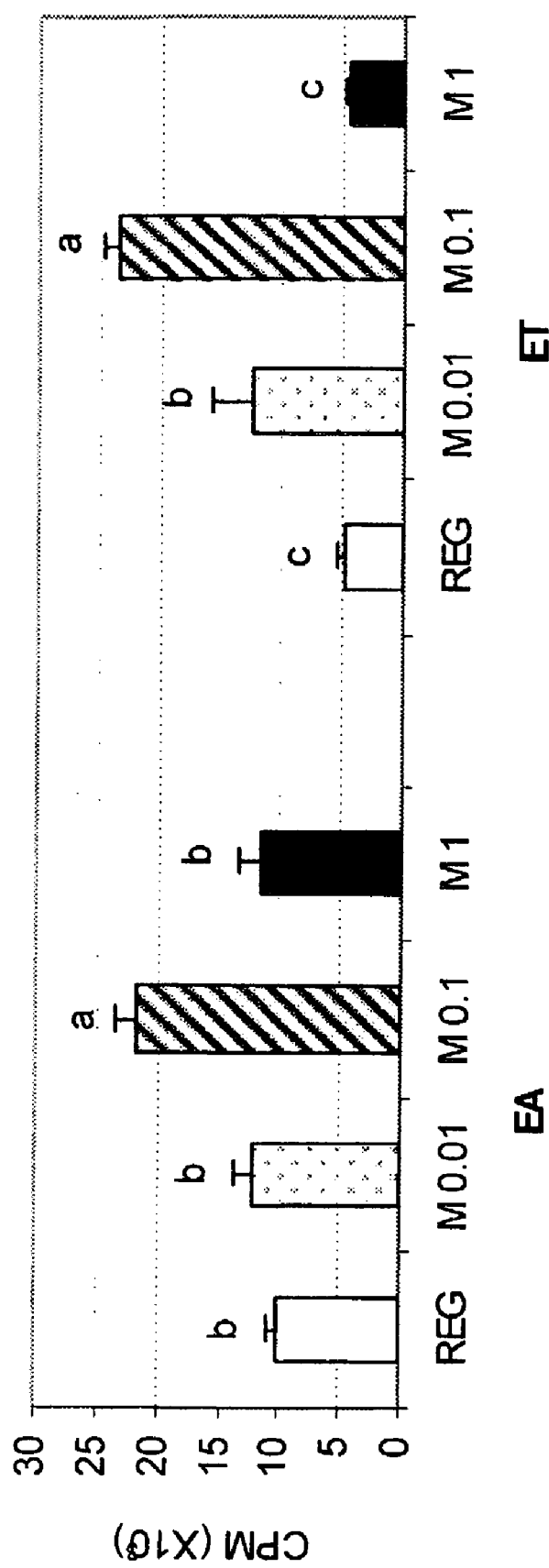
FIG. 6 is a graph showing the effect of probiotics on cellular immune response.

FIG. 6 shows Concanavaline A (Con A) induced proliferation of splenocytes from chickens following treatment with regular, 0.01%, 0.1% or 1.0% M: Mixtures of *P. acidilactici* and *S. boulardii* and infection with *Eimeria*. Birds were infected with 5,000 *E. acervulina* (EA) or *E. tenella* (ET) oocysts at day 14 post-hatch. Splenocytes were collected and cultured in the presence of Con A for 24 h. Cell proliferation was measured by [$^3$H]-thymidine assay. Each bar represents the mean±S.D. (N=3). Means lacking common superscripts differ in EA- or ET-infected chickens ($P<0.05$).

The proliferation responses in splenocytes stimulated with ConA in the birds fed regular or probiotic diets were used to determine systemic cellular immune responses against *Eimeria* in *P. acidilactici*-fed broiler chickens. In EA-infected birds, splenocytes of the 0.1% group exhibited significant ($P<0.05$) proliferation rates compared to all other groups including those on the regular and probiotic diets. In the ET-infected groups, 0.01% and 0.1% birds showed significantly ($P<0.05$) higher splenocyte proliferative responses to stimulation with Con A, with higher ($P<0.05$) proliferation rates in 0.1% than 0.01% birds (FIG. 6).

FIG. 7 shows fecal oocysts shed by birds infected with *E. acervulina* (EA). Oocysts were counted in fecal material collected 6-9 dpi with 5,000 *E. tenella* broiler chickens fed regular (REG), 0.1% (MG0.1) or 0.2% (MG0.2) MG: *P. acidilactici*-supplemented diets. Each bar represents the mean±S.D. (N=5 cages).

Figure 8:
FIG. 8 is a graph of fecal oocytes shed by birds infected by *E. acervulina* or *E. tenella*.

FIG. 8 shows fecal oocysts counted in fecal material collected 6-10 days past infection with 5,000 oocysts *E. acervulina* (EA) or *E. tenella* (ET) Broiler chickens were fed regular (REG), 0.01% (M0.01), 0.1% (M0.1) or 1.0% (M1.0) M at day 12 post-hatch. M indicates mixtures of *P. acidilactici* and *S. boulardii*. Each bar represents the mean±S.D. (N=5 cages).

Probiotics as alternative medicines for dogs with digestive disorders or dogs infected by infectious virus Applications of probiotics in dogs with digestive disorders The success of probiotics, MITOMAX™—mixtures of *P. acidilactici* and *S. boulardii*, in *Eimeria* infected broiler chickens led us to perform a field evaluation of canines with digestive disorders. MITOMAX™ is a trademark for probiotics owned by Imagilin Technology, LLC, Potomac, Md. for mixtures of *Pediococcus acidilactici* and *Saccharomyces cerevisiae boulardii* (*S. boulardii*) encapsulated in gelatin capsules. The collaborative field evaluations were performed by four veterinarians in three different animal hospitals located in Sao Paulo, Brazil (Table 2). The dogs' body weight ranged from 2 kg to 26 kg, and age ranged from 1 year old to 15 years old. The dogs suffered from different degrees of digestive disorders and were administered either one or two capsules of probiotics, depending on the dog's body weight. Within 14 days of treatment with probiotics, the dogs recovered from the digestive disorders and showed significant improvement. These results clearly show that probiotics have good effects on canines with digestive disorders.

TABLE 2

Field Evaluations of Probiotics on Dogs with Digestive Disorders in Animal Hospitals of Sao Paulo, Brazil

| Name | Ages (years) | Weight (Kgs) | Sex (M or F) | Symptoms (D, V, C, OC, F, LA)* before Probiotics treatment** | Length of Probiotics treatment (days) | Effects of Probiotics treatment |
|---|---|---|---|---|---|---|
| Fala Fino | 9 | 16 | F | D+ | 4 | Recovery OK |
| Peinrige | 4 | 10 | M | D+, V+, F+ | 4 | Recovery OK |
| Habil | 9 | 13 | F | OC | 10 | Improved |
| Beiney | 5 | 12 | M | D+, F++ | 9 | Recovery OK |
| Branea | 1 | 4 | F | LA+ | 4 | Improved |
| Pilly | 6 | 12 | M | OC+ | 9 | Improved |
| Focinha | 3 | 9 | M | LA+ | 4 | Improved |
| Nicole | 2 | 6 | F | D+, V+ | 4 | Improved |
| Togriho | 11 | 24 | M | LA+ | 9 | Improved |
| Tata | 10 | 5 | F | D++, F+ | 9 | Recovery OK |

TABLE 2-continued

Field Evaluations of Probiotics on Dogs with Digestive
Disorders in Animal Hospitals of Sao Paulo, Brazil

| Name | Ages (years) | Weight (Kgs) | Sex (M or F) | Symptoms (D, V, C, OC, F, LA)* before Probiotics treatment** | Length of Probiotics treatment (days) | Effects of Probiotics treatment |
|---|---|---|---|---|---|---|
| Rel Deigo | 10 | 25 | M | D+ | 15 | Recovery OK |
| Kate | 2 | 6 | F | D++++ | 7 | Recovery OK |
| Toli | 15 | 26 | M | D++, V++ | 4 | Recovery OK |
| Herna | 13 | 4 | M | D++ | 6 | Recovery OK |
| Mylon | 13 | 4 | M | D++ | 14 | Recovery OK |
| Hyuki | 10 | 4 | F | D++, V++, F+, LA+ | 9 | Recovery OK |
| Pelilico | 2 | 3 | M | D+, F+ | 12 | Recovery OK |
| Drojun | 1 | 7 | M | V+, D++ | 4 | Recovery OK |
| Max | 1 | 2 | M | D++++, F++ | 9 | Recovery OK |

*D: Diarrhea, V: Vomiting, C: Constipation, OC: Body Odor, F: Flatulence, LA: loss Appetite; ++++: very severe, +++: severe, ++: mild to severe, +: mild
**Probiotics treatment means oral administrated a capsule of MITOMAX ™-mixtures of *P. acidilactici* and *S. boulardii* per day for dog's body weight less than 20 kg, and two capsules of MITOMAX ™ per day for dog's body weight over 20 kg.

Probiotics as alternative medicine to stop bloody diarrhea of parvovirus-infected dogs.

Parvovirus-infected canines develop severe gastrointestinal distress such as vomiting and bloody diarrhea. Without proper treatment, parvovirus-infected dogs can die within a few days. No antibiotics can be applied to cure parvovirus-infected dogs since it is a viral infection. The recovery depends on the canines' ability to develop their own immune systems to fight against virus. This problem is a good candidate for us to apply probiotics to parvovirus-infected dogs. Four dogs diagnosed with parvovirus infection were shown to have bloody diarrhea even after treated with Normosol R, Reglan, Cefazolin, Metronidazole or Ampicillin, +/−Famotidine. Orally administered probiotics included mixtures of *P. acidilactici* and *S. boulardii*, and were given to the four dogs for two to three days. Not only did the bloody diarrhea stop, but also all four dogs had solid stool. No recurrence of bloody diarrhea was reported even after being released from hospital for two weeks as they continued the probiotics treatment (Table 3).

TABLE 3

Effects of probiotics on parvovirus infected dogs

| Name | Age (M) | Weight (Lbs) | Snap parvovirus test | Condition after standard treatment* | Length of Probiotics treatment | Effects of probiotics treatment** | Recurrence of diarrhea in 2 weeks |
|---|---|---|---|---|---|---|---|
| Cali | 4 | 11 | Positive | Bloody diarrhea, >6 times per day | 2 days | Diarrhea stop, solid stool | no |
| Denver | 5 | 14 | Positive | Bloody diarrhea, >6 times per day | 3 days | Diarrhea stop, solid stool | No |
| Flash | 12 | 45 | Positive | Bloody diarrhea, >6 times per day | 2 days | Diarrhea stop, solid stool | No |
| Molie | 9 | 45 | Positive | Bloody diarrhea, >6 times per day | 3 days | Diarrhea stop, solid stool | No |

: Performed by Dr. Volkenbourgh, DVM, at Animal Emergency Clinic, Lancaster, CA.
*Standard parvovirus treatment of the animal emergency clinic includes applying Normosol R, Reglan, Cefazolin, Metronidazole or Ampicillin, +/− Famotidine to the parvovirus infected dogs. Some also received hetastarch or a plasma transfusion.
**Probiotics treatment means oral administrated a capsule of MITOMAX ™-mixtures of *P. acidilactici* and *S. boulardii* per day The effects of probiotics on animals and humans are dependent on the viability of probiotics. Similar numbers of viable probiotics were detected from the encapsulated probiotics, *P. acidilactici*, stored for two years either at room temperature or at 4° C. No significant differences of morphology and body weight were observed by feeding *Eimeria*-infected broiler chickens with *P. acidilactici*, varying from 0.01% to 0.4%. Similar results were obtained when broiler chickens infected with *E. acervulina* or *E. tellena* were fed with mixtures of *P. acidilactici* and *S. boulardii* varying from 0.1% to 1%.

Effects of probiotics, either *P. acidilactici* or mixtures of *P. acidilactici* and *S. boulardii*, on *Eimeria*-infected broiler chickens were determined by 1) the reduction of oocysts isolated from the fecal samples, 2) stimulation of antibody production and 3) stimulation of proliferation of splenocytes. The clinic evaluation of probiotics clearly demonstrated that orally administrated mixtures of *P. acidilactici* and *S. boulardii* has improved the health conditions of canines with digestive disorders such as diarrhea, vomiting, appetite loss, and body odor. More importantly, canines suffering from bloody diarrhea caused by parvovirus infection showed recovery after treatment of orally administered mixtures of *P. acidilactici* and *S. boulardii* for two to three days. These results demonstrated that probiotics could be used as alternative medicines against infectious diseases.

Suitable probiotic microbes are yeast and lactic acid bacteria. Suitable probiotic bacteria are *Pediococcus, Lactobacillus, Bifidobacterium, Streptococcus*, and *Enterococcus*. Suitable yeast is *Saccharomyces cerevisiae boulardii*. The encapsulated probiotics are effective against gastrointestinal diseases caused by pathogenic bacteria, viruses, fungi, parasites and single-celled organisms. The encapsulated probiotics are effective against hookworms, roundworms, whipworms and tapeworms. The encapsulated probiotics are effective against coccidians, such as *Giardia*.

Encapsulated probiotics are effective against infectious gastrointestinal diseases in humans when humans with infectious gastrointestinal diseases ingest suitable dosages of encapsulated probiotics. Encapsulated probiotics are effective against infectious gastrointestinal diseases in fish when fish with infectious gastrointestinal diseases ingest suitable dosages of encapsulated probiotics. Probiotics in the form of dry powder are also effective with properties similar to those of encapsulated probiotics.

I claim:

1. A probiotic microbe composition comprising:
   at least one probiotic microorganism comprising *Pediococcus acidilactici* encapsulated in a mixture of xanthan gum and chitosan, the chitosan and xanthan gum being present in said mixture in an effective amount ranging from about 0.2-2.5% w/v of xanthan gum and about 0.1-1.0% w/v of chitosan.

2. A method of treating a gastrointestinal infectious disease by enhancing immune responses against antigens in a bird or a mammal, comprising:
   administering to the bird or mammal infected with said infectious disease an effective amount for said treating of a composition comprising at least one probiotic microorganism comprising *Pediococcus acidilactici* encapsulated in a mixture of about 0.2-2.5% w/v of xanthan gum and about 0.1-1.0% w/v of chitosan, wherein said infectious disease is caused by protozoa, pathogenic bacteria, fungi, parasites, or a virus selected from the group consisting of parvovirus, rotavirus, and influenza virus.

3. The method of claim 2, wherein the bird is selected from the group consisting of a chicken, a parrot, a parakeet, a pigeon, a turkey, a duck, and a goose.

4. The method of claim 2, wherein the mammal is selected from the group consisting of a dog, a cat, a guinea pig, a hamster, a mouse, a rabbit, a monkey, a chimpanzee, a pig and a human.

5. The method of claim 2 wherein the parasites are selected from the group consisting of hookworms, roundworms, whipworms and tapeworms.

6. The method of claim 2 wherein the protozoa are selected from the group consisting of *Eimeria, Giardia, Cryptosporidum, Toxoplasma, Plasmodium, Leishmania*, and *Cyclospora*.

7. The method of claim 2 wherein said treating of the infected bird or mammal modulates the immune responses of the infected bird or mammal by increasing antibody production or increasing T-cell or helper T-cell proliferation in the infected host.

8. The method of claim 2, wherein the composition further comprises *Saccharomyces* yeast.

9. The method of claim 2, wherein the composition is administered in combination with an antibiotic.

* * * * *